United States Patent [19]

Charbonnier et al.

[11] Patent Number: 4,840,177

[45] Date of Patent: Jun. 20, 1989

[54] CURRENT-BASED DEFIBRILLATOR

[75] Inventors: Francis M. Charbonnier, McMinnville; Martin G. Rockwell, Sherwood; Carl E. Benvegar, Corvallis, all of Oreg.

[73] Assignee: Hewlett-Packard Company, Palo Alto, Calif.

[21] Appl. No.: 117,125

[22] Filed: Nov. 3, 1987

[51] Int. Cl.$^4$ .............................................. A61N 1/36
[52] U.S. Cl. ................................. 128/419 D; 128/734
[58] Field of Search ........................... 128/419 D, 734

[56] References Cited

U.S. PATENT DOCUMENTS

| | | | |
|---|---|---|---|
| 3,860,009 | 1/1975 | Bell et al. | 128/419 D |
| 4,077,413 | 3/1978 | Partridge | 128/419 D |
| 4,119,903 | 10/1978 | Pirkle | 128/419 D |
| 4,233,659 | 11/1980 | Pirkle | 128/419 D |
| 4,303,075 | 12/1981 | Heilman et al. | 128/419 D |
| 4,328,808 | 5/1982 | Charbonnier et al. | 128/419 D |
| 4,574,810 | 3/1986 | Lerman | 128/419 D |
| 4,771,781 | 9/1988 | Lerman | 128/419 D |

OTHER PUBLICATIONS

Monzon et al., "Current Defibrillator: New Instrument of Programmed Current for Research and Clinical Udse", IEEE Transactions on Biomedical Engineering, vol. BME-32, No. 11, Nov. 1985, pp. 928-934.
Kerber et al., "Advance Prediction of Transthoracic Impedance in Human Defibrillation and Cardioversion: Importance of Impedance in Determining the Success of Low-Energy Shocks," Cardiovascular Center, University of Iowa Hospital, vol. 70, No. 2, Aug. 1984, pp. 303-308.
Jones et al., "Determining Transthoracic Impedance, Delivered Energy, and Peak Current During Defibrillation Episodes," Medical Instrumention, vol. 15, No. 6, Nov.-Dec. 1981, pp. 380-382.
Kerber et al., "Automated Impedance-Based Energy Adjustment for Defibrillation: Experimental Studies," Laboratory Investigation, vol. 71, No. 1, Jan. 1985, pp. 136-140.

Primary Examiner—Ruth S. Smith

[57] ABSTRACT

A method and apparatus is disclosed for providing to the body of a patient a defibrillation pulse having a magnitude calculated to induce in that particular patient a desired defibrillation current. The patient's response to a defibrillation pulse is characterized in advance of defibrillation by repeatedly sampling the patient's transthoracic impedance to a small alternating current excitation signal. The sample having the lowest magnitude is taken to represent the patient's true transthoracic impedance. This lowest sampled impedance value is normalized to take into account the shape of the expected waveform and is then multiplied by the desired current to yield the target charge level to which an energy storage device must be charged to induce the desired current to flow in the patient on discharge. Charging of the energy storage device desirably begins before measurement of transthoracic impedance is completed and continues until the target charge is reached. Discharge of an energy storage device so charged causes the desired current to flow through the patient.

9 Claims, 3 Drawing Sheets

CURRENT-BASED DEFIBRILLATOR

BACKGROUND

1. Field of Invention

The present invention relates generally to the field of cardiac defibrillation and in particular to a method and apparatus for applying to the body of a patient a voltage calculated to induce in that particular patient a desired defibrillation current.

2. Description of the Prior Art

A defibrillator is a device used to administer a high voltage shock pulse through a pair of electrodes, or "paddles," to the chest of a patient in cardiac arrest. A selected, discrete quantity of energy is stored in a capacitor and is then electrically discharged into the patient through the paddle circuit. In prior art devices, the quantity of energy is typically selected on the basis of patient size, weight and condition.

The success achieved with such prior art devices has been variable. While an energy of 150 joules might successfully defibrillate one patient, another ostensibly comparable patient may not respond until the energy level is raised to 360 joules. The risk of damage to the myocardium from large defibrillation shocks dictates that defibrillation should be attempted with the lowest energy practicable. However, delays associated with charging the defibrillator to successively higher energy levels if lower energy pulses fail increase the risk of patient brain damage due to oxygen deprivation.

The differing responses of patients to a given defibrillation pulse is believed attributable, in significant part, to patients' differing transthoracic impedances. Transthoracic impedance is the term given the load resistance presented by a patient at the paddles during defibrillation and determines, inter alia, the fraction of energy stored in the storage capacitor that is actually delivered to the patient. One type of known defibrillator, shown in U.S. Pat. No. 4,328,808, is able to compute the transthoracic impedance of the patient being defibrillated from measured pre- and post-discharge parameters. This information can be used by the operator as an aid in selecting the energy of a second defibrillation pulse if the first pulse proves ineffective.

In an article by Kerber et al. entitled "Automated Impedance-Based Energy Adjustment for Defibrillation: Experimental Studies," Circulation, Vol. 71, No. 1, pp. 136-140 (1985), there is described an experimental animal defibrillator in which transthoracic impedance is detected in advance of defibrillation by using a low current A.C. sampling signal. The defibrillation energy level selected by the operator is automatically increased, generally by a factor of two, if the detected patient impedance exceeds 70 ohms. Although an improvement over prior systems, the Kerber et al. system still suffers from a number of deficiencies making it poorly suited for clinical application.

Principal among the deficiencies of the Kerber et al. system is its lack of control over current delivered to the patient. Our work has indicated that defibrillation success as a function of current is optimized in humans about a narrow range of current values for a given pulse shape. For a pulse duration of four milliseconds, the optimum current is approximately 30 amperes. Currents only slightly below this value have a much poorer success rate. The magnitude of transthoracic impedance encountered in typical patients, however, ranges from approximately 15 to 150 ohms, a 10 to 1 ratio, rendering the delivery of an optimum current unlikely if the defibrillator can only alter the operator-selected energy to a single other value.

Accordingly, a need exists for a defibrillation method and apparatus that permits selection of a determined defibrillation current for a patient in cardiac arrest, irrespective of the magnitude of that patient's transthoracic impedance.

SUMMARY

The primary objective of the present invention, therefore, is to deliver to a patient a defibrillation pulse having a magnitude calculated to induce in that particular patient a desired defibrillation current.

Another object of the present invention is to characterize in advance of defibrillation a patient's transthoracic impedance and to automatically tailor the magnitude of a defibrillation pulse accordingly.

A further object of the present invention is to provide an accurate measurement of transthoracic impedance upon which a computation of an appropriate storage capacitor charge can be based.

In accordance with the preferred embodiment of the present invention, a method and apparatus is provided for characterizing in advance of defibrillation the response of a patient to a defibrillation pulse and determining therefrom the voltage that must be applied to the patient to induce a desired defibrillation current to flow. The patient's response to a defibrillation pulse is characterized by repeatedly sampling the patient's transthoracic impedance to a small alternating current excitation signal. The impedance sample having the lowest magnitude is taken to represent the patient's true transthoracic impedance, with a higher values being attributed to varying degrees of patient contact resistance.

The lowest sampled impedance is normalized to take into account the shape of the expected waveform with which the stored charge will be delivered. In defibrillators employing a capacitor as the energy storage device, this normalized factor is multiplied by the desired current to yield a target voltage level to which the capcitor must be charged to induce the desired current to flow in the patient on discharge. If a different form of energy storage device is used, a different scaling factor is used to relate patient impedance to energy storage requirements. Charging of the capacitor desirably begins before the measurement of transthoracic impedance is completed and continues until the target voltage level is reached. Discharge of a capacitor so charged causes the desired current flow through the patient.

These and other objects, features and advantages of the present invention will be more readily apparent from the following detailed description of a preferred embodiment thereof, which proceeds with reference to the accompanying drawings.

DESCRIPTION OF PREFERRED EMBODIMENT

Figure 1:
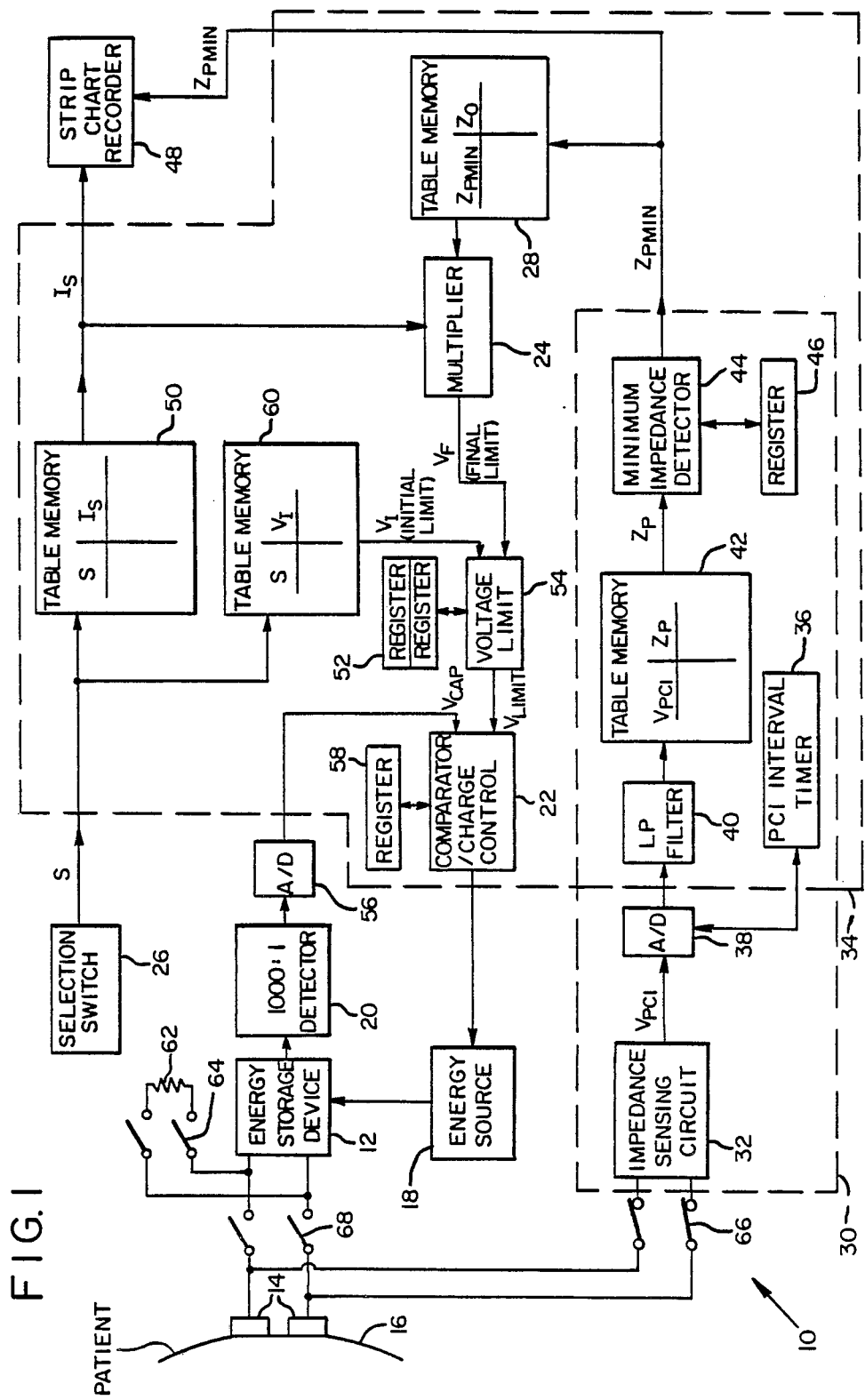
FIG. 1 is a functional block diagram illustrating the preferred embodiment of the present invention.

FIG. 1 is a functional block diagram illustrating the basic arrangement of a current-based defibrillator 10 in accordance with the preferred embodiment of the present invention. The apparatus includes an energy storage device 12 such as a capacitor, paddles 14 for applying an electrical shock from the capacitor to a patient 16 and an energy source 18 for charging the capacitor. A detector 20 detects the charge accumulated by the capacitor and feeds this data back to a comparator/charge control circuit 22 which controls the capacitor's charging accordingly.

Charging of the capacitor continues until the voltage across the capacitor reaches a target value. This target value is determined by a multiplier 24 which multiplies the magnitude of current desired to be delivered to the patient, $I_s$, by a normalized impedance factor, $Z_o$. $I_s$ is selected by the operator using a selector switch 26. $Z_o$ is retrieved from a look-up table 28 in response to transthoracic impedance measurements made by an impedance measurement system 30.

Impedance measurement system 30 includes an impedance sensing circuit 32 that excites the patient with a low current A.C. excitation signal through paddles 14 and produces a corresponding output signal related to the patient's transthoracic impedance at the excitation signal frequency. In the preferred embodiment, the excitation signal has a frequency of 31 kilohertz, a frequency at which the patient's transthoracic impedance closely approximates the patient's impedance to a high current defibrillation pulse. In alternative embodiments, however, other excitation signal frequencies can be used and the non-linear correspondence with the patient's response to a high current defibrillation pulse can be reflected in the scaled impedance factors stored in look-up table 28.

Impedance sensing circuit 32 is connected to paddles 14 by relay contacts 66. The relay is arranged so that relay contacts 66 are closed when relay contacts 68, connecting the energy storage capacitor to the paddles, are open, and vice versa. Relay contacts 66 are normally closed at all times except when the storage capacitor is actually being discharged into the patient.

Figure 2:
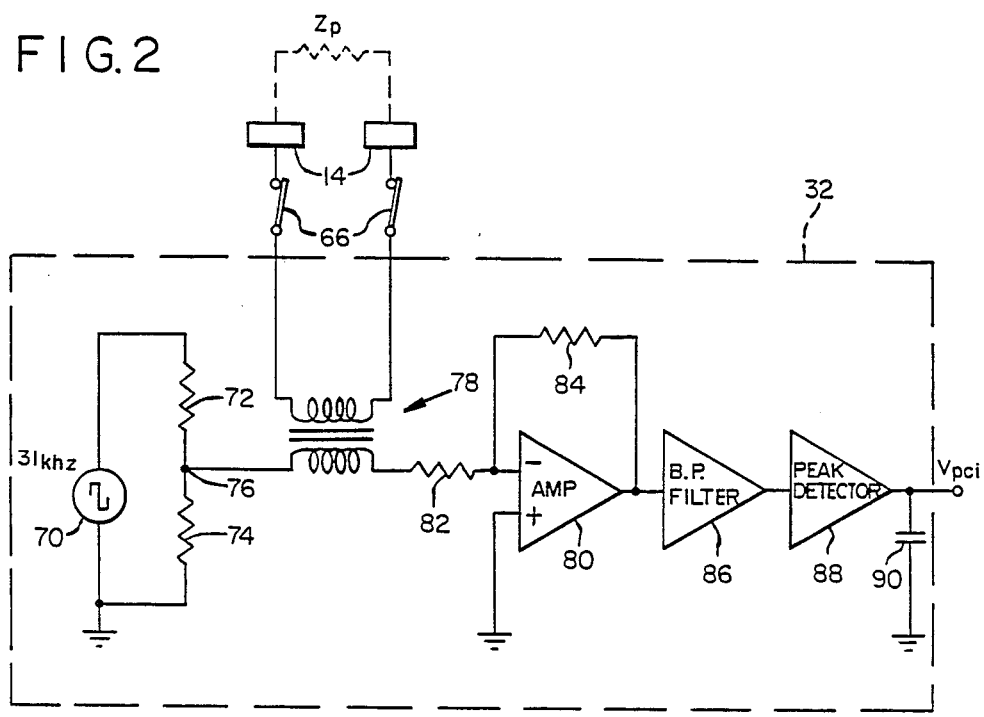
FIG. 2 is a functional block diagram of the impedance sampling circuit included in FIG. 1.

Impedance sensing circuit 32 is shown in more detail in FIG. 2. A 31 kilohertz, five volt peak-to-peak square wave signal generator 70 drives a voltage divider comprised of resistors 72 and 74 to produce a 25 millivolt (peak-to-peak) signal at circuit node 76. This 25 millivolt signal is applied to the primary winding of an isolation transformer 78, the secondary of which is connected to defibrillator paddles 14 through relay contacts 66.

The patient impedance between paddles 14 is reflected across transformer 78 and becomes an element of the gain setting circuitry of a high gain amplifier 80. With resistors 82 and 84 having values of 31.6 and 1210 ohms respectively, the gain of amplifier 80 equals $1210/(31.6+Z_r)$ where $Z_r$ is the magnitude of the impedance reflected from the patient across the primary winding.

The output of amplifier 80 is fed to the input of a band pass filter 86 which extracts and amplifies the fundamental frequency component of the 31 kilohertz square wave, yielding a sine wave at its output. This sine wave output signal has an amplitude which is a function of the impedance between paddles 14. The output of filter 86 is then input to a peak detector 88 which stores the peak value on a capacitor 90.

The foregoing arrangement provides a continuous voltage signal corresponding inversely to the patient's transthoracic impedance. This relationship is non-linear and is empirically characterized for a given implementation. In the illustrated embodiment, an output of four volts corresponds to a patient impedance of 0 ohms and an output of 0.125 volts corresponds to a patient impedance of 255 ohms. This relationship can also be derived from the gain characteristics of amplifier 80, filter 86 and peak detector 88.

The analog signal at the output of impedance sensing circuit 32 is provided to an eight bit analog-to-digital converter 38, such as a National Semiconductor type ADC-0844, which periodically samples the analog signal and converts each sample into digital form. If the signal provided to converter 38 has a magnitude of less than 1.25 volts, it is desirably amplified by an additional factor of four. Such amplification provides two additional data bits of digital resolution for low amplitude signals.

The frequency at which A/D converter 38 samples the output of impedance sensing circuit 32 is dictated by an associated single board computer (SBC) 34 and is approximately 240 hertz in the preferred embodiment. Computer 34 is built around an Intel 8052 microprocessor and 8K of associated ROM and implements many of the subsequent processing functions illustrated in FIG. 1. The A/D sampling continues during a predetermined measurement period, here termed the patient contact indication (PCI) interval, the length of which is set by a software implemented decrementing timer 36 in computer 34. This period is typically about two seconds, a period long enough to yield approximately 500 impedance samples.

The samples output from A/D converter 38 are provided to single board computer 34 for further processing. The first processing step is to low pass filter the digitized voltage using a software implemented filter 40 to remove the 20 to 40 millivolts of noise that may be impressed on this signal. The filtered, digitized voltage signal is then used to index a first look-up table 42 that correlates the output from A/D converter 38 to the patient's transthoracic impedance.

First look-up table 42, together with the other look-up tables illustrated in FIG. 1, are implemented using the ROM memory associated with single board computer 34. Table 42 is arranged in two segments, with the second segment relating to those signals from A/D converter 38 which have been amplified by an additional factor of four to provide increased resolution. A total of approximately 500 pairs of entries are provided in this first table memory.

Each transthoracic impedance value retrieved from first look-up table 42 is compared by a minimum impedance detector 44 against a minimum impedance value, $Z_{pmin}$, stored in a register 46 in the microprocessor. This register is initially loaded with a value of 255 ohms (FF hex). Thereafter, as each of the impedance values is retrieved from table 42, it is compared with the register value. If a sampled impedance value is lower than the previously stored minimum, the register is loaded with the new minimum value. At the end of the two second PCI interval, this $Z_{pmin}$ register contains the lowest impedance value sampled during the interval. This impedance value is sent to a strip chart recorder 48 for display. The minimum sampled impedance value obtained by this technique is believed more accurately to reflect the patient's true transthoracic impedance, with higher sampled values being attributed to poorer contact between the paddles and the patient.

At the conclusion of the two second sampling interval, the lowest transthoracic impedance value detected is used as an index into a second look-up table memory 28. Look-up table 28 provides a normalized impedance factor $Z_o$ as its output that is used to compute the capacitor charge needed to deliver the desired current to the patient, taking into account the shape of the defibrillation pulse's waveform.

It will be recognized that the energy stored in storage capacitor 12 is solely a function of the voltage on the capacitor and its capacitance, by the formula $E = \frac{1}{2} CV^2$. The peak current delivered to the patient on discharge of the capacitor, however, depends in large part on the shape of the waveform with which this energy is delivered. The shape of the waveform depends, inter alia, on the capacitance, inductance and resistance of the discharge path. The resistance of the discharge path includes not only the transthoracic impedance of the patient but also the loss resistance of the defibrillator itself, about eleven ohms in the illustrated embodiment. The normalized impedance factor provided by look-up table 28 thus reflects the correlation between peak delivered current as a function of patient impedance for the particular characteristics of the defibrillator's discharge path. This correlation can be established empirically or by resort to mathematical modelling of the discharge circuit.

The normalized impedance factor output from second look-up table 28 is provided to a first input of a multiplier stage 24. A signal responsive to selector switch 26 is provided to the multiplier's second input.

Selector switch 26, by which the operator selects the desired defibrillation current, $I_s$, provides a four-bit digital signal to the input of a third look-up table 50. Third look-up table 50 converts the setting of switch 26 into an 8-bit digital signal representing the selected current to be delivered to the patient. This is the signal applied to the second input of multiplier 24. The multiplication of the 8-bit current signal from third look-up table 50 with the 8-bit normalized impedance factor signal from second look-up table 28 yields a 16-bit output signal representing the final target voltage to which capacitor 12 is to be charged. This sixteen bit result is stored in two eight bit voltage limit registers 52 associated with a voltage limit stage 54.

Capacitor 12 is charged to the voltage limit stored in register 52 by an energy source 18. Energy source 18 can comprise a conventional flyback charger in which a 14 volt DC battery source is applied to one end of a transformer winding and the bottom end of that winding gated on and off to ground. Suitable chargers are described in U.S. Pat. No. 4,233,659 and 4,119,903, both to Pirkle and assigned to the present assignee.

The charge on capacitor 12 is sampled through a 1000 to 1 voltage divider network 20 and is converted into digital form by a second analog-to-digital converter 56. Second A/D converter 56 is actually a second channel of the National Semiconductor ADC 0844 circuit employed for first A/D converter 38. Again, like the first A/D converter, the analog voltage applied to the input of second A/D converter input is multiplied by a factor of four if its magnitude is less than 1.25 volts. By this technique, increased resolution of low voltages is provided.

The output from second A/D converter 56 is periodically stored in a capacitor voltage register 58 and is compared by comparator/charge control circuit 22 against the limit voltage value stored in voltage limit registers 52. As long as the capacitor's voltage is less than this stored limit, capacitor charge control 22 allows energy source 18 to continue charging the capacitor. When however, the sampled capacitor voltage equals or exceeds the limit voltage, charging is terminated.

To expedite charging of storage capacitor 12, it is generally desirable to begin the charging operation before the patient's transthoracic impedance, and consequently the final limit voltage, have been determined. To accomplish this, the patient is initially assumed to have an arbitrary transthoracic impedance and charging is begun towards a corresponding voltage limit. In the preferred embodiment, this initial voltage limit is provided by a fourth look-up table 60 based on a presumed 50 ohm impedance and on the particular current selected. The resultant initial voltage limit is stored in the microprocessor's voltage limit registers 52 for the two seconds of the PCI interval. After the impedance measurement is completed and the final voltage limit has been determined, that final value is substituted for the initial value in the voltage limit registers.

In certain unusual instances, the charge provided to storage capacitor 12 during the two second PCI interval may exceed the charge that is ultimately determined to be required. This may be the case if, for example, the patient's transthoracic impedance is on the order of 20 ohms, a value which would correspond to a relatively low capacitor charge. In such instance, excess charge may be bled off storage capacitor 12 and dissipated in a resistor 62 through a relay circuit 64 connected to the storage capacitor. Second A/D converter 56 and comparator/charge control 22 monitor this discharging of the capacitor and interrupt it when the desired capacitor voltage has been reached.

Figure 3:
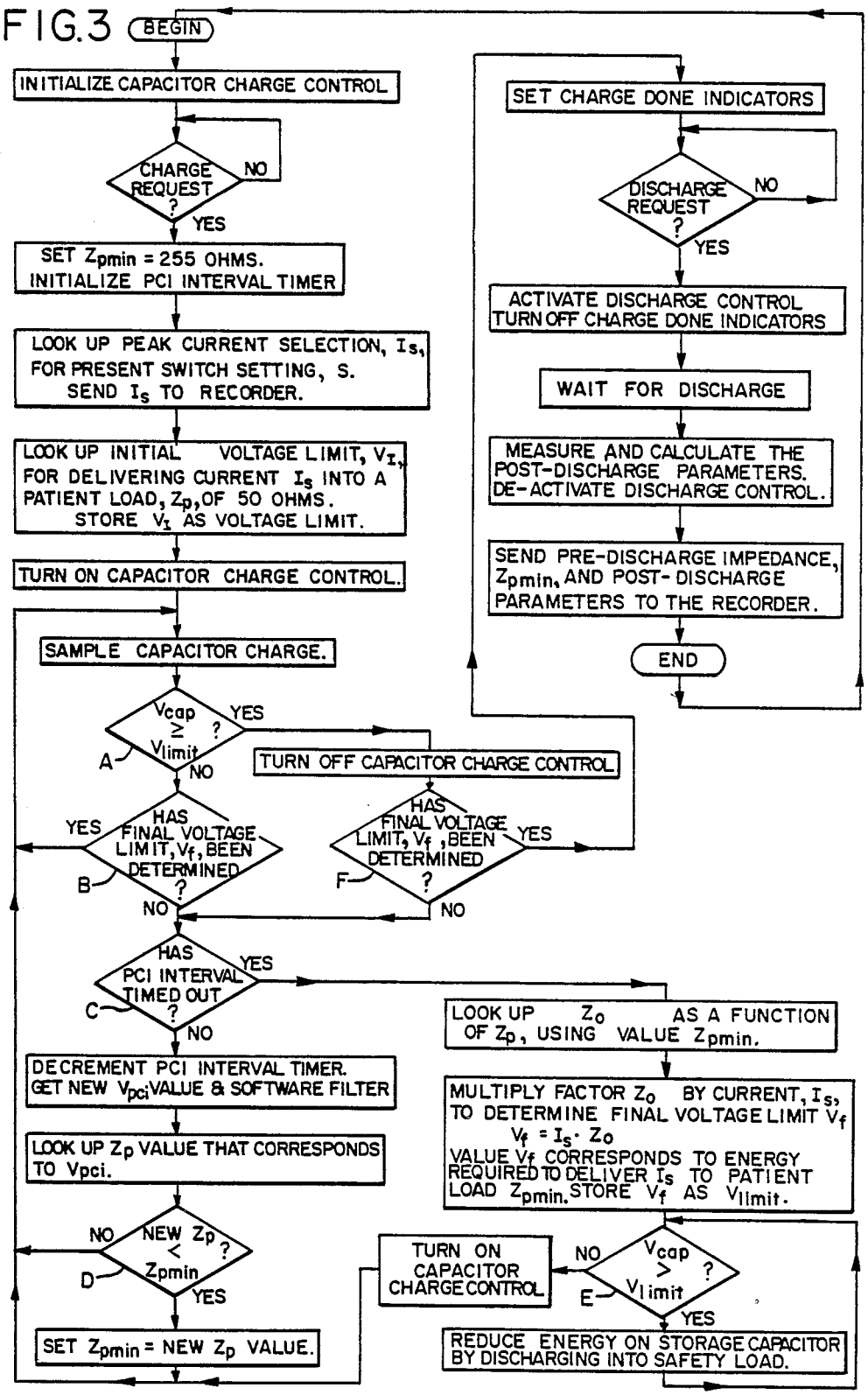
FIG. 3 is a flow chart detailing the sequence of steps executed by the embodiment of FIG. 1.

FIG. 3 is a flow chart detailing the various sequences of steps executed by the above-described embodiment of the present invention.

When the instrument is activated, capacitor charge control 22 and voltage limit circuit 54 are reset, resetting the capacitor limit voltage stored in voltage limit registers 52 to zero. When selection switch 26 is operated to initiate circuit operation, an initial $z_{pmin}$ value of 255 ohms is loaded in minimum impedance register 46 and PCI contact interval timer 36 is initialized to a two second time period. The current $I_s$ corresponding to the selection on switch 26 is then retrieved from third look-up table 50 and is sent to strip chart recorder 48 for display. The initial voltage limit corresponding to the selected current is retrieved from fourth look-up table 60 and is stored in voltage limit registers 52. Capacitor comparator/charge control circuit 22 is then activated.

As the first step in the primary processing loop, second A/D converter 56 provides to comparator/charge control circuit 22 a digital representation of the capacitor voltage. This value is stored in capacitor voltage register 58 and is compared with the limit voltage stored in voltage limit registers 52, as illustrated by block A of FIG. 2. If the capacitor voltage is less than this limit, the process proceeds to block B to check whether the final voltage limit has yet been determined. If it has not, the process proceeds to block C to examine whether the two second PCI interval has yet expired. If it has not, PCI interval timer 36 is decremented and a new transthoracic impedance sample is taken. The resultant impedance value provided by first look-up table 42 is compared against the previously stored minimum impedance value $z_{pmin}$ in block D. If it is less than the previously stored minimum value, the old minimum value is replaced by the new value and the processing loop repeats, comparing the capacitor voltage with the limit voltage.

The above-described loop repeats itself at a rate of approximately 240 hertz until the two second PCI timer 36 has timed out. At this point, the process branches from block C and determines the normalized impedance factor $Z_o$ corresponding to the lowest impedance value $Z_{pmin}$ sampled during the two second interval. Normalized impedance factor $Z_o$ is provided to multiplier 24 where it is multiplied by the magnitude of $I_s$ to determine the final limit voltage $V_f$. This final limit voltage is substituted in voltage limit registers 52 which previously contained the initial limit voltage.

The process then checks, in block E, whether the voltage accumulated on capacitor 12 during the two second impedance measuring interval is greater than the final limit voltage which has just been determined. If so, the capacitor is connected through relay contacts 64 to discharge load 62 to bleed off the excess charge. When the charge bleeds down to he desired final voltage, the process returns to block A.

At block A, the voltage on the capacitor is again examined. This time through the loop, the final voltage limit has been determined, so block B causes the process to loop indefinitely, comparing the voltage on the capacitor with the final limit voltage until the limit voltage is reached. At this point, charging of capacitor 12 is discontinued.

It may happen that the voltage limit initially stored in voltage limit registers 52 is reached before the final voltage limit has been determined. In this case, charging is interrupted and the process loops idly through block F until the final voltage limit is determined. If, after the final voltage limit is determined, it is found at block A to be greater than the initial voltage limit which has already been reached, charging will resume until the new, final voltage limit is reached.

After the charge on the capacitor has reached the final voltage limit, the process escapes from the charging loop at block F. The apparatus then sets a ready indicator and awaits a discharge request. If any charge is lost from the capacitor due to the capacitor's internal leakage resistance while awaiting a discharge request, a trickle charge circuit (not shown) restores the lost charge.

When a discharge request is received, relay contacts 66 open and relay contacts 68 close, discharging capacitor 12 through the patient. The peak instantaneous current actually delivered to the patient is detected by a current sampling loop (not shown) and the associated energy delivered and patient impedance are calculated using known techniques. These parameters are then sent to strip chart recorder 48 for display.

Having described and illustrated the principles of our invention in a preferred embodiment, it should be apparent to those skilled in the art that the invention can be modified in arrangement and detail without departing from such principles. For example, while the current delivered to the patient in the illustrated embodiment is controlled by limiting the charge accumulated in the capacitor, the same result can be achieved by providing a current limiting resistance in the capacitor discharge path. Similarly, while the preferred embodiment has been phrased in terms of charging a capacitor up to a desired charge, the same result can be achieved by discharging a fully charged capacitor down to the desired point. It will also be apparent that the energy storage means employed need not be a capacitor. The principles of the invention are equally applicable to inductive storage media, in which defibrillation energy is stored in a magnetic field, and to superconducting storage media, in which defibrillation energy is stored as a continuously circulating current. In view of the many alternative embodiments to which the principles of the present invention can be applied, we claim as our invention all modifications as may come within the scope and spirit of the following claims and equivalents thereof.

We claim:

1. A defibrillator system for delivering an electrical shock to a patient to restore normal cardiac rhythm comprising;
   a capacitor for accumulating an electrical charge;
   first and second electrodes for applying an electrical shock from the capacitor to the patient;
   charging means for charging the capacitor;
   detector means for detecting the charge accumulated by the capacitor;
   impedance measuring means for determining a transthoracic impedance of the patient, said impedance measuring means including means for sampling the patient's transthoracic impedance periodically;
   current establishing means for establishing a fixed magnitude of current which is desired to be delivered to the patient irrespective of the patient's transthoracic impedance; and
   circuit means cooperating with the charging means, detector means, impedance measuring means and current establishing means for discontinuing the charging of the capacitor when the accumulated charge is sufficient to deliver the selected current to a patient having the measured transthoracic impedance, said circuit means including processing means for determining the charge accumulation required to deliver the desired current to a patient having a transthoracic impedance equal to the lowest value of transthoracic impedance sampled.

2. A defibrillator comprising:
   storage means for storing energy;
   first and second measuring electrodes;
   impedance sensing means for applying a low amplitude current from said measuring electrodes to the patient's chest during a measurement interval to develop thereby a first signal related to the impedance presented across said electrodes by the patient's chest as a function of time during said interval;
   first processing means for processing said first signal to produce a second signal related to the minimum impedance presented across said electrodes during said measurement interval;
   second processing means for determining from said second signal the magnitude of voltage to which the storage means must be charged to deliver to said patient a desired defibrillating current;
   means for providing the storage means with the voltage charge determined by the second processing means; and
   means for discharging said storage means through said patient.

3. The defibrillator of claim 2 in which said first processing means comprises:

sampling means for periodically sampling said first signal to obtain a plurality of instantaneous signal values, each of said values being indicative of the impedance across the measuring electrodes at a particular instant during the measurement interval; and examining means for examining each said sample value to determine whether it is indicative of an impedance lower than the other the sample values.

4. The defibrillator of claim 3 in which the sampling means includes means for producing a digital representation of each sample value and in which the examining means includes means for comparing each digital representation of a sample value against a current-minimum sample value stored in a digital memory.

5. A defibrillator comprising:

storage means for storing energy;

first and second measuring electrodes;

impedance sensing means for applying a low amplitude current from said electrodes to the patient's chest to develop thereby a signal related to the impedance presented across said electrodes;

first processing means including an analog-to-digital converter for converting the signal developed by the impedance sensing means into digital form, said first processing means further including means for amplifying said signal prior to digitizing if the amplitude of said signal is below a predetermined threshold, said amplification increasing thereby the digital resolution of low amplitude signals provided by said analog to digital converter;

second processing means for determining from the digitized signal the magnitude of voltage required on the storage means to deliver a desired defibrillating current to the patient;

means for providing the storage means with the voltage charge determined by the second processing means; and means for discharging the energy stored in said storage means through said patient.

6. A defibrillator comprising:

storage means for storing energy;

sensing means for applying a low amplitude current to the chest of the patient and for determining from the response of the patient thereto the magnitude of voltage required on the storage means to deliver a desired current to the patient, said sensing means operating during an initial, measurement phase of the defibrillator's operation;

means for setting a desired initial voltage limit towards which the storage means can be charged during said measurement phase;

means for initiating the charging of the storage means during said measurement phase;

means for discontinuing the charging of the storage means during said measurement phase if the voltage on the storage means reaches said desired initial voltage limit; and means for discharging the storage means through the patient.

7. The defibrillator of claim 6 which further includes means for reinitiating the charging of the storage means at the conclusion of the measurement phase if the magnitude of voltage determined by the sensing means to be required on the storage means exceeds the initial voltage to which the storage means has been charged.

8. The defibrillator of claim 6 which further includes means for bleeding charge from the storage means at the conclusion of the measurement phase if the magnitude of voltage determined by the sensing means to be required on the storage means is less than the initial voltage to which the storage means has been charged.

9. In a defibrillation method that includes the steps of detecting a patient's transthoracic impedance and providing a corresponding, "target" electrical charge to a storage medium, said target charge being selected in response to the detected transthoracic impedance so as to provide a desired defibrillation current to the patient upon discharge of the storage medium through the patient, an improvement comprising the steps:

charging the storage medium to a charge greater than the target charge; and bleeding charge from the storage medium until the target charge is reached.

* * * * *